United States Patent [19]

Hashimoto et al.

[11] 4,320,225

[45] Mar. 16, 1982

[54] PERIANDRINS EXTRACTED FROM PLANTS OF THE GENUS PERIANDRA

[75] Inventors: Yohei Hashimoto, 44, Kasumi-Cho 5-Chome, Nishinomiya-Shi, Hyogo-Ken, Japan; Masaru Ogura, Choshi; Hiroyuki Ishizone, Koganei, both of Japan

[73] Assignees: Yamasu Shoyu Kabushiki Kaisha, Chiba; Yohei Hashimoto, Hyogo, both of Japan

[21] Appl. No.: 219,538

[22] Filed: Dec. 23, 1980

Related U.S. Application Data

[63] Continuation-in-part of Ser. No. 90,308, Nov. 1, 1979, abandoned, which is a continuation-in-part of Ser. No. 28,800, Apr. 10, 1979, abandoned.

[30] Foreign Application Priority Data

| Apr. 14, 1978 | [JP] | Japan | 53/43198 |
| Jan. 9, 1979 | [JP] | Japan | 54/404 |
| Jan. 9, 1979 | [JP] | Japan | 54/405 |
| Mar. 2, 1979 | [JP] | Japan | 54/23413 |

[51] Int. Cl.$^3$ ............... C07H 15/20; C07H 15/24
[52] U.S. Cl. .................................. 536/4; 424/180
[58] Field of Search ....................... 536/4, 17 R

[56] References Cited

U.S. PATENT DOCUMENTS

| 3,629,231 | 12/1971 | Hough et al. | 536/4 |
| 3,940,381 | 2/1976 | Boissevain | 536/4 |
| 4,112,218 | 9/1978 | Inoue et al. | 536/4 |

OTHER PUBLICATIONS

Machado, A., Chemical Abstracts, vol. 36, Abstract No. 3319, 1942.

*Primary Examiner*—Blondel Hazel
*Attorney, Agent, or Firm*—Wenderoth, Lind & Ponack

[57] ABSTRACT

The sweet-tasting substances contained in the roots of plants of the genus Periandra were isolated and found to consist essentially of four species of novel glycosides, which were respectively named Periandrins I, II, III and IV. The Periandrins are defined by chemical formulas as well as their physical and chemical properties and are useful, for example, as natural sweetening agents.

7 Claims, 4 Drawing Figures

PERIANDRINS EXTRACTED FROM PLANTS OF THE GENUS PERIANDRA

CROSS REFERENCE TO RELATED APPLICATIONS

This is a continuation-in-part of application Ser. No. 090,308, filed Nov. 1, 1979 now abandoned, which in turn is a continuation-in-part of application Ser. No. 28,800, filed Apr. 10, 1979 now abandoned.

FIELD OF THE INVENTION

This invention relates to periandrins which are novel natural sweet-tasting substances.

The plants of the genus Periandra are the leguminous shrubs which grow wild in the northern and middle parts of Brazil. In these native localities, the roots of these plants are called "Alcacus de terra," which means "native licorice" in English, and have been used from ancient times for medical use and the like for purposes such as expectoration. The roots of these plants possess sweetness as well as a considerable degree of bitterness. Thus, the extracts obtained by extracting the above-mentioned roots with water, an alcohol, etc. could not be used, as they are, for sweeteners or sweetener aids such as licorice extracts.

Incidentally, it has been reported that the sweet-taste component present in the roots of the Periandra plants is glycyrrhizin (Chemical Abstracts Vol. 36, p. 3319, 1942).

SUMMARY OF THE INVENTION

The present inventors have undertaken intensive research on the sweet-tasting substances contained in the roots of Periandra plants and have succeeded in isolating the sweet substances of the following four species, which have been named Periandrins I, II, III and IV, repectively.

The periandrins provided by the present invention are represented by the following formula (A), wherein the substituent R is given in the following description and each M which is in the sugar moiety and which is also found in the moiety R is hydrogen or a cation substantially non-toxic to humans.

(A)

The Periandrin I is a substance in which the substituent R in the formula (A) is represented by the following formula.

The Periandrin II is a substance in which the R in the formula (A) is represented by the following formula.

The Periandrin III is a substance in which the R in the formula (A) is represented by the following formula.

The Periandrin IV is a substance in which the R in the formula (A) is represented by the following formula

BRIEF DESCRIPTION OF THE DRAWINGS

In the drawings.

The samples of Periandrins I and II are in the free-acid form, and the samples of Periandrins III and IV are in the mono-ammonium salt form.

DETAILED DESCRIPTION OF THE INVENTION

Chemical structures and physical and chemical properties of Periandrins I, II, III and IV

The periandrins provided in accordance with the present invention are glycosides represented by the following formula, wherein there are four Periandrins I through IV with respect to the substituent R.

(A)

In the formula (A), each M which is in the sugar moiety and which is also found in the moiety R as shown hereinbelow is hydrogen or a cation substantially non-toxic to humans such as a monovalent cation such as an alkali metal, e.g., Na and K, or ammonium or calcium.

Periandrin I

Periandrin I in its free-acid form (M=H) has the following physical and chemical properties.

(a) Melting point: >300° C. (turning black in the vicinity of 190° C.)

(b) Specific rotation: $[\alpha]_D^{20} -23.0°$ (C=1.0, water)

(c) Molecular weight: 822 (FD mass spectrometric analysis, $M^+.H.Na=846$)

(d) Elemental analysis: $C_{42}H_{62}O_{16}.4H_2O$ Found: C 56.52%, H 7.61%. Calculated: C 56.36%, H 7.88%.

Figure 1:
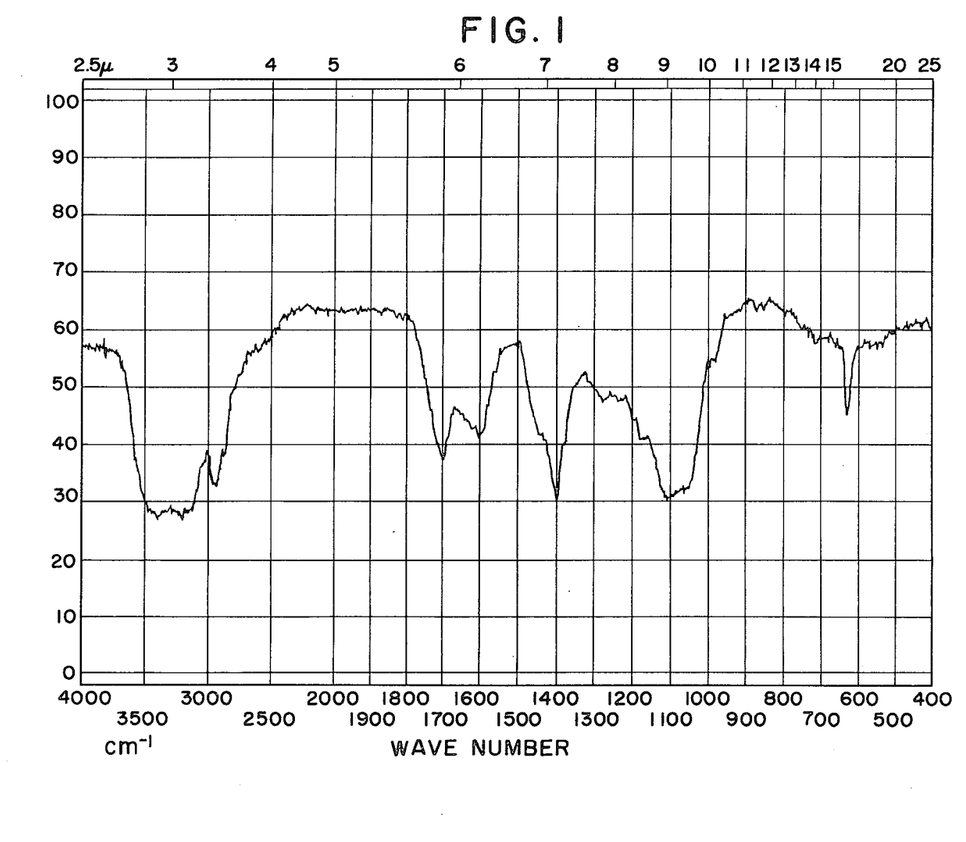
FIGS. 1 through 4 are spectral diagrams respectively indicating the infrared absorption spectra of Periandrins I through IV.

(e) Compositional formula: $C_{42}H_{62}O_{16}$ (f) Infrared absorption spectrum: $\nu_{max}^{KBr}$ 3400, 3200, 1700, 1600, 1400, 1100, 625 cm$^{-1}$ (cf. FIG. 1)

(g) Solubilities: very soluble in water; soluble in pyridine; slightly soluble in methanol and ethanol (h) Thin-layer chromatography (1) n-butanol-benzene-methanol-28% ammonia water=4-3-2-3 Rf value 0.18

(2) methylene chloride-methanol-ethanol-40% acetic acid=8-4-1-2 Rf value 0.44

(3) ethyl acetate-n-propanol-water=7-5-4 Rf value 0.17

(i) Ultraviolet absorption spectrum: endabsorption (j) Appearance: colorless rectangular plate crystals (water-methanol mixed solvent)

Periandrin II

Periandrin II is a substance represented by the following formula, in which M has been defined hereinbefore.

Periandrin II

Periandrin II in its free-acid form (M=H) has the following physical and chemical properties.

(a) Melting point: 216° to 220° C. (decomposed)

(b) Specific rotation: $[\alpha]_D^{28} +37.0°$ C. (C=0.27, water)

(c) Elemental analysis: $C_{42}H_{62}O_{16}.3H_2O$
Found: C, 57.93% H, 7.80%. Calculated: C, 57.52% H, 7.82%.

Figure 2:
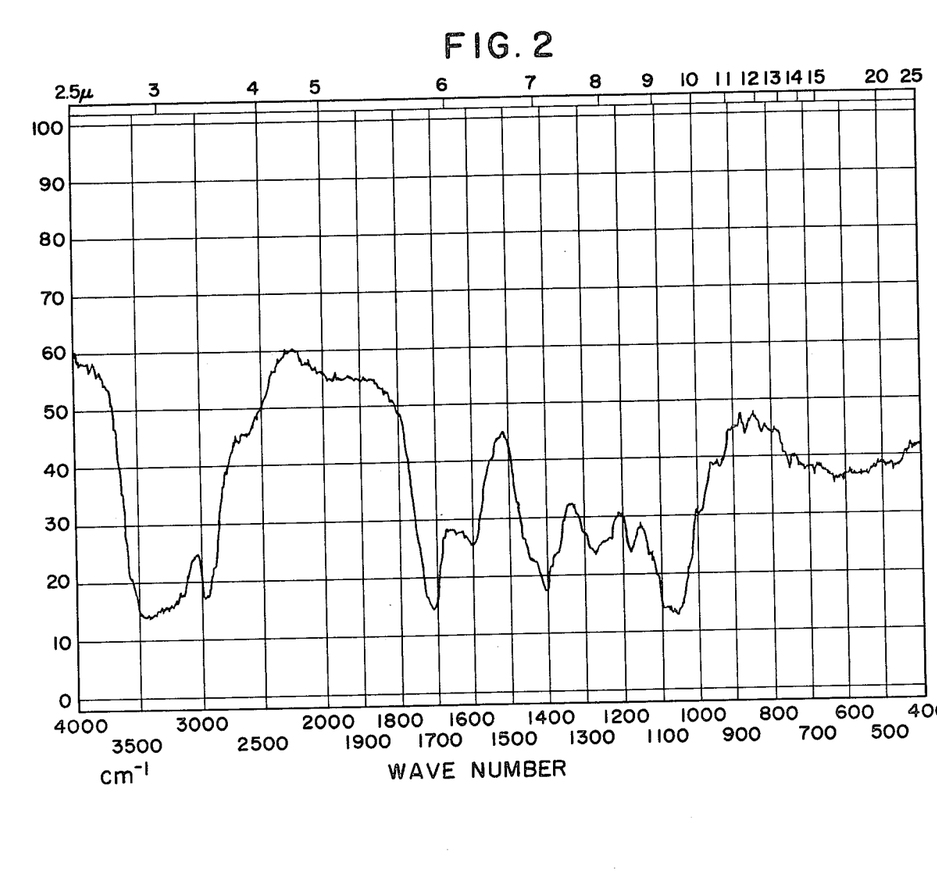

(d) Compositional formula: $C_{42}H_{62}O_{16}$ (e) Infrared absorption spectrum: $\nu_{max}^{KBr}$ 3400, 3200, 2950, 1710, 1600, 1400, 1060 cm$^{-1}$ (cf. FIG. 2)

(f) Solubilities: very soluble in water; soluble in pyridine; slightly soluble in methanol and ethanol.

(g) Thin-layer chromatography (1) n-butanol-benzene-methanol-28% ammonia water=4-3-2-3 Rf value 0.18

(2) methylene chloride-methanol-ethanol-40% acetic acid=8-4-1-2 Rf value 0.44

(3) ethyl acetate-n-propanol-water=7-5-4 Rf value 0.21

(h) Ultraviolet absorption spectrum: endabsorption (i) Appearance: colorless rectangular plate crystals (water-methanol mixed solvent)

Periandrin III

Periandrin III is a substance represented by the following formula, in which M has been defined hereinbefore.

Periandrin III

Periandrin III in its free-acid form (M=H) has the following physical and chemical properties.

(a) Melting point: >300° C.

(b) Specific rotation: $[\alpha]_D^{18} -24.5°$ (C=1.1, water)

(c) Elemental analysis: $C_{42}H_{64}O_{16}\cdot 2H_2O$ Found: C 58.07%, H 8.17%. Calculated: C 58.59%, H 7.96%.

Figure 3:
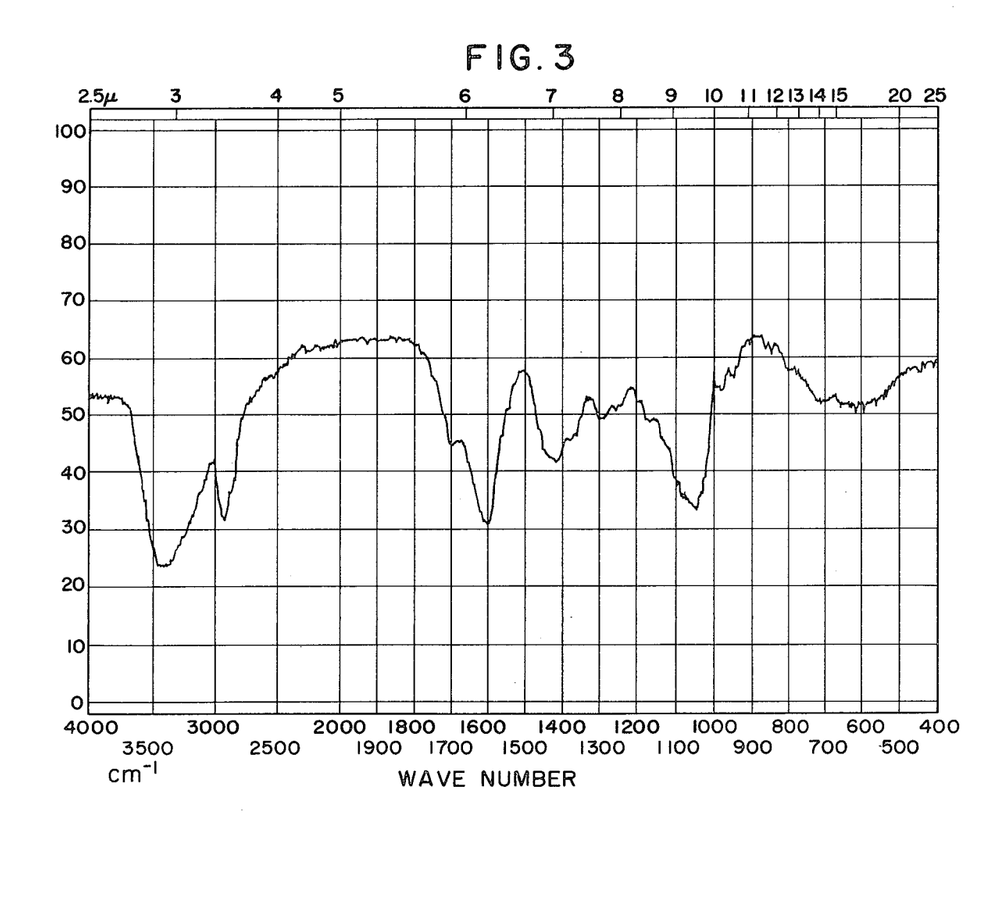

(d) Compositional formula: $C_{42}H_{64}O_{16}$ (e) Infrared absorption spectrum: $\nu_{max}^{KBr}$ (the mono-ammonium salt) 3400, 2930, 1700, 1600 1408, 1040 cm$^{-1}$ (cf. FIG. 3)

(f) Solubilities: very soluble in water; soluble in pyridine; slightly soluble in methanol and ethanol (g) Thin-layer chromatography (1) n-butanol-benzene-methanol-28% ammonia water=4-3-2-3 Rf value 0.15

(2) methylene chloride-methanol-ethanol-40% acetic acid=8-4-1-2 Rf value 0.40

(3) ethyl acetate-n-propanol-water=7-5-4 Rf value 0.14

(h) Ultraviolet absorption spectrum: endabsorption (i) Appearance: colorless crystalline powder Periandrin IV Periandrin IV is a substance represented by the following formula, in which M has been defined hereinbefore.

Periandrin IV

Periandrin IV in its free-acid form (M=H) has the following physical and chemical properties.

(a) Melting point: >300° C.

(b) Specific rotation: $[\alpha]_D^{22} +96°$ (C=2.5, water)

(c) Elemental analysis: $C_{42}H_{64}O_{16}\cdot 3H_2O$ Found: C 57.01%, H 7.70%. Calculated: C 57.39%, H 8.03%.

Figure 4:
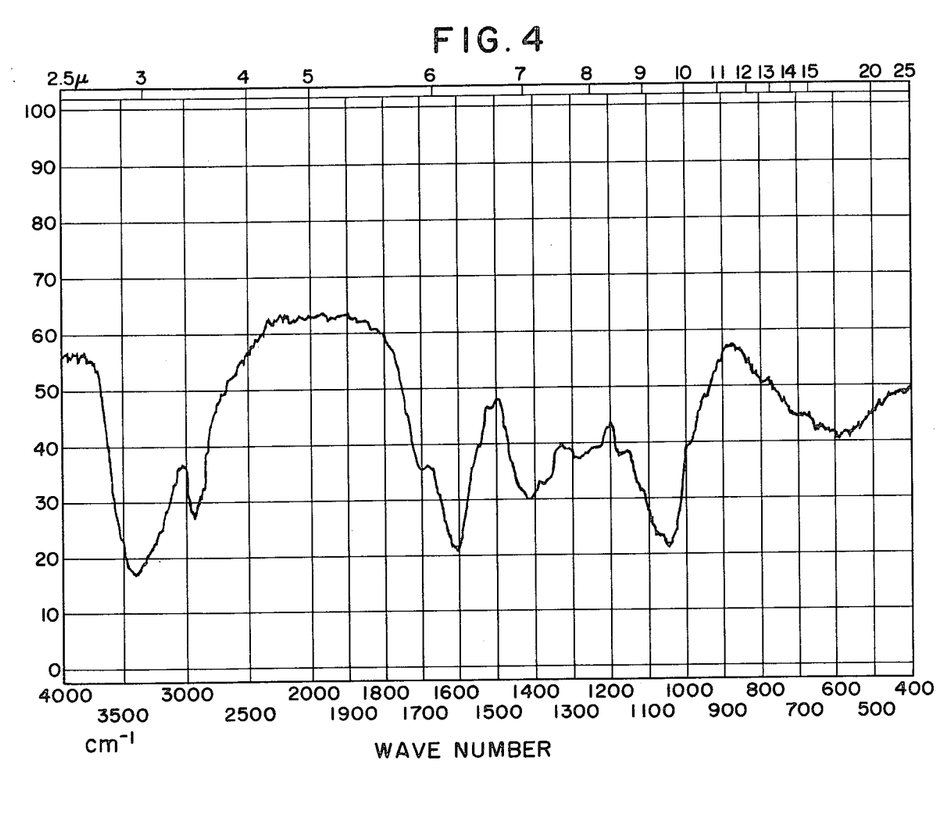

(d) Compositional formula: $C_{42}H_{64}O_{16}$ (e) Infrared absorption spectrum: $\nu_{max}^{KBr}$ (the mono-ammonium salt) 3400, 2920, 1700, 1600 1407, 1045 cm$^{-1}$ (cf. FIG. 4)

(f) Solubilities: very soluble in water; soluble in pyridine; slightly soluble in methanol and ethanol (g) Thin-layer chromatography (1) n-butanol-benzene-methanol-28% ammonium water=4-3-2-3 Rf value 0.15

(2) methylene chloride-methanol-ethanol-40% acetic acid=8-4-1-2 Rf value 0.40

(3) ethyl acetate-n-propanol-water=7-5-4 Rf value 0.19

(h) Ultraviolet absorption spectrum: endabsorption (i) Appearance: colorless crystalline powder Extraction and purification of periandrins Periandrins are present in the roots of the plants of the genus Periandra, which are typically represented by Periandra mediteranea, Periandra dulcis, etc. The roots of these plants or these roots in dried state are subjected to extraction of the periandrins, if desired, after they have been chipped or ground.

The extraction is generally carried out by employing, as an extracting reagent, (i) water or a water-hydrophilic or water-miscible organic solvent containing not more than about 80% of a hydrophilic or water miscible organic solvent (such as methanol, ethanol, propanol, butanol, acetone, and methyl ethyl ketone) under the condition of a pH not lower than 3, or (ii) a water-containing or aqueous hydrophilic organic solvent (such as ethanol containing not more than 15% of water) under an acidic condition of a pH lower than 3.

The temperature for the extraction is not especially restricted, and can be in the range of higher than the freezing point of the extracting reagent and lower than its boiling point. Under the condition of a low temperature, there is an advantage in that the resulting extract is accompanied by a smaller amount of impurities although a longer time is required for leaching. Under the condition of a high temperature, the period of time for the extraction is advantageously shortened. The period of time for extraction can be optionally selected in accordance with the type of extracting reagent, temperature for extraction and other conditions. The efficiency of extraction can be increased by incorporating alkalis, polyphosphates and/or surface active agents into the extracting reagent.

The isolation and purification of periandrins from the resulting extract can be carried out by combining suitably conventional purification methods such as (a) an acid precipitation method, (b) a method of extraction with water-containing or aqueous acidic hydrophilic or water-miscible organic solvents of a pH lower than 3, (c) a precipitation method using hydrophilic or water-miscible organic solvents of a pH not lower than 3, (d) a method of fractionation by ion-exchange or adsorption chromatography, (e) a method of treatment with molecular sieve membrane or dialysis membrane, and (f) a recrystallization method. The outlines of the typical purification methods are given below.

Periandrins are precipitated from their aqueous solution systems under acidic conditions of a pH lower than 3. In this case, the major parts of the bitter substance contaminating the extract remain in the solution as they are. When mineral acids such as hydrochloric acid and sulfuric acid are added to the aqueous solution which has been directly prepared from the extract to carry out acid-precipitation treatment, periandrins are precipitated together with proteins and various acid-insoluble substances.

In order to reduce the coprecipitation of proteins and the like, it is also possible to resort, depending on the necessity, to pretreatment steps such as (i) a method of decomposing the acid-insoluble substances such as proteins into acid-soluble peptides or amino acids according to a treatment with enzymes such as protease, (ii) a method of heating the proteins at a temperature of 70° C. or higher to coagulate and remove them, and (iii) a method of adding to the solution metal hydroxides such as calcium hydroxide, magnesium hydroxide and aluminium hydroxide or first adding to the solution inorganic salts of these metals and then adjusting the solution to an alkaline pH to form a metal hydroxide in the solution whereby proteins are precipitated and removed. In the case of the acid precipitation treatment, the yield of precipitate may be increased by the salt-out effect in the presence of neutral salts such as sodium chloride, sodium sulfate, sodium nitrate, sodium formate and sodium acetate.

Under the pH conditions in the range of weak acidity of a pH of 3 or higher to alkalinity, the solubility of periandrins with respect to a solution containing about 85% or more hydrophilic or water miscible organic solvents is low, but the bitter substances are soluble therein, whereby the periandrins and bitter-taste substances can be separated. Thus, a periandrin can be separated and collected as a precipitate by adding a hydrophilic or water-miscible organic solvent in an amount such as 85% or more, preferably 95% or more, to the aqueous extract, the concentrated solution or solid of the separated and purified extract solution, or the solution prepared by neutralizing and dissolving the precipitate of the above-mentioned acid precipitation step. A periandrin can also be obtained as a precipitate from the extract obtained according to the extracting method with water-containing hydrophilic organic solvents of a pH lower than 3, by simply adjusting the pH of the extract to 3 or higher with alkalis.

Since a periandrin is soluble at a pH lower than 3 in water-containing (or aqueous) hydrophilic (or water-miscible) organic solvents such as an aqueous ethanol, the aqueous extract is concentrated and adjusted to an acidic pH or the precipitate formed by the above-mentioned acid precipitation treatment is collected and, if necessary, adjusted to an acidic pH, and then hydrophilic organic solvent is added thereto in such an amount as to cause the concentration to be 85% or higher, preferably 95% or higher. Periandrins can be thus extracted. As a method of preparing an aqueous solution of a periandrin from the resulting extract, insoluble residues are removed from the extract and (1) the extract, as it is or after the concentration, is suspended in water and then dissolved through neutralization thereof or (2) to the extract are added non-hydrophilic (or water-immiscible) organic solvents which are miscible with hydrophilic or water-miscible organic solvents to produce a periandrin as a precipitate which is then dissolved in water.

Periandrins can be isolated from other contaminants, or periandrins themselves can also be separated from one another, by subjecting a solution containing periandrins to fractional adsorption treatment or fractional elution treatment with the carriers of ion-exchangers such as weakly basic anion-exchange resins and DEAE-crosslinked dextran, or adsorbents such as synthetic adsorbents, silica gel, granular polyamides, activated carbon, activated alumina, activated clay, and diatomaceous earth. These treatments can be generally carried out with column-chromatography methods, and their operations and conditions can be selected and established suitably in accordance with the types of the carriers used and other factors.

Specific examples of purification are described below.

EXAMPLE OF PURIFICATION 1

Twenty (20) kgs. of the root of *Periandra dulcis* was chipped into small pieces and subjected to extraction for one day with 100 liters of water at a temperature of 70° to 80° C. The extraction was repeated twice and the extract was filtered. The filtrates were combined and concentrated under reduced pressure to 8 liters. To the concentrated liquid was added an 11-fold volume of ethanol (88 liters) with stirring, and the mixture was left to cool overnight at 5° C. The separated precipitate (1.06 kg) was collected by filtration and again dissolved in 4 liters of water. To this solution was further added an 11-fold volume of ethanol (44 l.) with stirring, and the mixture was left to cool at 5° C. overnight.

The same operation was repeated again and 870 g of a crude sweet-tasting fraction was obtained. The crude sweet-tasting fraction was purified by silica gel column chromatography. More particularly, 150 g of the crude sweet-tasting fraction was adsorbed onto an equivalent amount of silica gel ("Kieselgel 60" supplied by Merck & Co. Inc.), which was then charged onto a column (6 cm in diameter, 70 cm in length) that had been prepared beforehand with 1 kg of silica gel. The sweet-tasting fraction was eluted with a mixed solvent comprising n-butanol, benzene, methanol and 28% ammonia water (mixing ratio 4-3-2-2). Thus were obtained a fraction containing Periandrins I and II and a fraction containing Periandrins III and IV.

The fraction containing Periandrins I and II was subjected to silica gel chromatography treatment repeatedly (2 to 3 times) with the above-mentioned mixed solvent, until the Periandrins I and II exhibited a single spot respectively on a thin-layer chromatography (developing solvent: methylene chloride-methanol-ethanol-40% acetic acid=8-4-1-2, and ethyl acetate-n-propanol-water=7-5-4). After the resulting substances were confirmed to be a single substance respectively on the thin-layer chromatography, 860 mg of Periandrin I and 240 mg of Periandrin II were obtained as crystals from hot acetic acid or a water-alcohol mixed solvent, respectively.

The fraction (1.1 g) containing Periandrins III and IV was adsorbed on an equivalent amount of silica gel, which was then charged onto a column (6 cm in diameter, 70 cm in length) that had been previously prepared with 1 kg of silica gel. The column was subjected to elution with a mixed solvent consisting of chloroform, methanol and water (mixing ratio=25-17-3). The eluent was subjected to silica gel chromatography treatment repeatedly (2 to 3 times), until Periandrins III and IV exhibited a single spot respectively on a thin-layer chromatography (developing solvent: methylene chloride-methanol-ethanol-40% acetic acid=8-4-1-2, and ethyl acetate-n-propanol-water=7-5-4). After the resulting substances were confirmed to be a single substance respectively on the thin-layer chromatography, 40 mg of Periandrin III and 19 mg of Periandrin IV were obtained as crystalline powder from water, respectively.

EXAMPLE OF PURIFICATION 2

Thirty (30) kgs. of the root of *Periandra dulcis* was chipped into small pieces and subjected to extraction for one day at room temperature with 150 liters of ca. 94% ethanol which had been adjusted to a pH of 2.0 to 2.5 with hydrochloric acid. The extraction was repeated twice and the extract was filtered. The filtrates were combined, neutralized with an alkali, and concentrated to 6 liters under reduced pressure. To the concentrated liquid was added an 11-fold volume of ethanol (66 lit.) with stirring, and the mixture was left to cool at 5° C. overnight. The separated precipitate was collected by filtration and again dissolved in 3 liters of water. To the solution was further added an 11-fold volume of ethanol (33 lit.) with stirring, and the mixture was left to cool at 5° C. overnight. The resulting precipitate (430 g) was collected by filtration.

The crude sweet-tasting fraction thus obtained was purified by silica gel-column chromatography. More particularly, 100 g of the crude sweet-tasting fraction was adsorbed onto an equivalent amount of silica gel ("Kieselgel 60" supplied by Merck & Co., Inc.), which was then charged onto a column (4.5 cm in diameter, 80 cm in length) that had been prepared beforehand with 500 g of silica gel. The sweet-tasting fraction was eluted with a mixed solvent comprising n-butanol, benzene, methanol and 28% ammonia water (mixing ratio 4-3-2-2). Thus, a fraction containing Periandrins I and II and a fraction containing Periandrins III and IV were obtained.

The fraction containing Periandrins I and II was repeatedly subjected to silica gel chromatography treatment (1 to 2 repetitions) with the above-mentioned mixed solvent, until the Periandrins I and II exhibited a single spot respectively on a thin-layer chromatography (developing solvent: methylene chloride-methanol-ethanol-40% acetic acid=8-4-1-2, and ethyl acetate-n-propanol-water=7-5-4). After the resulting substances were confirmed to be a single substance respectively on the thin-layer chromatography, 700 mg of Periandrin I and 170 mg of Periandrin II were obtained as crystals from hot acetic acid or a water-alcohol mixed solvent, respectively.

The fraction (1.5 g) containing Periandrins III and IV was adsorbed on an equivalent amount of silica gel, which was then charged onto a column (4.5 cm in diameter, 90 cm in length) that had been previously prepared with 600 g of silica gel. The column was subjected to elution with a mixed solvent comprising chloroform, methanol and water (mixing ratio=25-17-3). The eluent was subjected to repetitions (1 to 2 times) of silica gel chromatography treatment until Periandrins III and IV exhibited a single spot respectively on a thin-layer chromatography (developing solvent: methylene chloride-methanol-ethanol-40% acetic acid=8-4-1-2, and ethyl acetate-n-propanol-water=7-5-4). After the resulting substances were confirmed to be a single substance on the thin-layer chromatography, 23 mg of Periandrin III and 9 mg of Periandrin IV were respectively obtained as crystalline powder from water.

Periandrins possess a sweet taste which is refreshing and delicate. The results of tests on the degree of sweetness are shown in the following test example.

TEST EXAMPLE

As series of standard sweet liquids, five classes of the aqueous solutions containing 0.3 g/100 ml, 0.5 g/100 ml, 1 g/100 ml, 2 g/100 ml and 3 g/100 ml of sucrose were prepared. Separately, aqueous solutions containing 10 mg/100 ml and 20 mg/100 ml of Periandrins I through IV were respectively prepared. As controls, the aqueous solutions containing 10 mg/100 ml and 20 mg/100 ml of glycyrrhizin (supplied by Tokyo Kasei, Japan) were employed.

The degrees of sweetness of these aqueous solutions containing sweet-tasting components were evaluated in comparison with the sucrose solution series by a panel of fifteen judges. The degree of sweetness as a multiple of that of sucrose was calculated as the average of values judged by the panel. The results are shown in Table 1.

TABLE 1

| Solutions containing sweet components | | Sucrose equivalent concentration | Degree of sweetness (multiple of sucrose sweetness) |
|---|---|---|---|
| Periandrin I | 10mg/100ml | 0.90 | 90 |
|  | 20mg/100ml | 1.57 | 78.3 |
| Periandrin II | 10mg/100ml | 0.95 | 95 |
|  | 20mg/100ml | 1.53 | 76.5 |
| Periandrin III | 10mg/100ml | 0.92 | 92 |
|  | 20mg/100ml | 1.64 | 82 |
| Periandrin IV | 10mg/100ml | 0.85 | 85 |
|  | 20mg/100ml | 1.60 | 80 |
| Glycyrrhizin | 10mg/100ml | 0.93 | 93 |
|  | 20mg/100ml | 1.40 | 70 |

As is apparent from Table 1, periandrins have substantially the same sweetness as glycyrrhizin. With respect to the comparison of sweetness, periandrins possess very weak or no bitter taste, whereas glycyrrhizin has a bitter taste. It was also found that the sweetness of periandrins was sensed more quickly. Thus, periandrins are quite useful as natural sweetening agents of good quality.

In the above examples, the thin-layer chromatography was carried out on silica gel ("Kiesel gel 60 F254" supplied by Merck & Co., Inc., U.S.A.).

What is claimed is:

1. A periandrin which is a glycoside represented by the formula wherein R is a substituent selected from the group consisting of substituents respectively represented by the formulas:

(I)

(II)

(III); and

(IV)

where each M is selected from the group consisting of hydrogen and cations substantially non-toxic to humans.

2. Periandrin I as set forth in claim 1, in which the substituent R in the formula is represented by the formula

3. Periandrin II as set forth in claim 1, in which the substituent R in the formula is represented by the formula 4. Periandrin III, as set forth in claim 1, in which the substituent R in the formula is represented by the formula 5. Periandrin IV as set forth in claim 1, in which the substituent R in the formula is represented by the formula 6. The periandrin as set forth in any one of the preceding claims, in which M is hydrogen.

7. The periandrin as set forth in any one of claims 1 to 5, in which M is a cation selected from the group consisting of alkali metal ions, ammonium, and calcium ion.

* * * * *